United States Patent [19]

Inoue et al.

[11] Patent Number: 4,653,502

[45] Date of Patent: Mar. 31, 1987

[54] ELECTRODE SECUREMENT SHEET

[75] Inventors: Hirokatsu Inoue, Chiba; Chuji Shimizu, Funabashi, both of Japan

[73] Assignee: Fukuda Denshi Co., Ltd., Tokyo, Japan

[21] Appl. No.: 809,701

[22] Filed: Dec. 17, 1985

[30] Foreign Application Priority Data

Jan. 22, 1985 [JP] Japan .............................. 60-6902[U]

[51] Int. Cl.⁴ .............................................. A61B 5/04
[52] U.S. Cl. ................................................... 128/640
[58] Field of Search ............................. 128/639–641, 128/644, 783, 798, 802, 803

[56] References Cited

U.S. PATENT DOCUMENTS

| | | | |
|---|---|---|---|
| 3,545,432 | 12/1970 | Berman | 128/640 |
| 3,741,219 | 6/1973 | Sessions | 128/803 |
| 4,300,575 | 11/1981 | Wilson | 128/802 |
| 4,331,153 | 5/1982 | Healy | 128/641 |
| 4,370,984 | 2/1983 | Cartmell | 128/803 X |
| 4,401,125 | 8/1983 | Taylor et al. | 128/639 |

Primary Examiner—Lee S. Cohen
Attorney, Agent, or Firm—Pollock, VandeSande & Priddy

[57] ABSTRACT

An electrode securement sheet for securing, to the skin surface of a living body, an electrode held in close contact with the skin surface for deriving a weak current from the living body, is disclosed. The sheet comprises a substantially circular electrode securement section, which is to be secured to the skin surface to cover the electrode. A lead securement section extends integrally from the electrode securement section for securing, to the skin surface, a lead for leading the weak current extracted through the electrode to an electrocardiogram. A lead securement piece is provided separate from the electrode securement section and lead securement section, these sections being separably bonded to a cardboard.

5 Claims, 7 Drawing Figures

PRIOR ART

ELECTRODE SECUREMENT SHEET

BACKGROUND OF THE INVENTION

1. Field of the Invention

This invention relates to an electrode securement sheet for securing an electrode to a living body skin surface in close contact therewith.

2. Prior Art

As is well known in the art, electricity is induced in the living body by the activity of the heart, brain, muscles, etc.

Particularly, electricity produced by the activity of the heart is detected as weak current induced on the surface of the skin of the living body, using an external electrocardiogram to check for abnormality of the heart. To this end, electrodes of an input section of the electrocardiogram are held in close contact with the skin surface of, and thereby electrically coupled to, the living body.

FIGS. 5 to 7 show a prior art electrode that is held in close contact with the skin surface for current derivation. FIG. 5 shows the electrode 7 in perspective. The electrode 7 has a substantially circular sticky sheet piece 8. The sticky sheet piece 8 has a doughnut-like cloth piece having a central opening 9, and its lower surface has enough stickiness to be held in close contact with the skin surface M of the living body as shown in FIG. 7.

An electrode plate engagement member 10 made of a hard synthetic resin is bonded to the upper surface of the sticky sheet piece 8 to close the opening 9. The electrode plate engagement member 10 has a magnetic lead coupler 11 projecting from the upper surface. As shown in FIG. 7, an electrode plate 12, which is held in close contact with the skin surface M of the living body to derive a weak current from the heart, is secured to the lower surface of the lead coupler 11.

FIG. 6 is a back view of a lead connector 13, through which a weak current or voltage derived from the heart through the electrode plate 12 is led via a lead to an electrocardiogram installed in a room. The lead connector 13 has substantially the same size as the electrode 7 and is made of a hard resin. It has a recess 14, and a magnetic electrode coupler 15 is provided in the recess 14 and secured to the lead connector 13. One end of a lead 6 is connected to the electrode coupler 15, and its other end is connected to the electrocardiogram.

To obtain an electrocardiograph using the electrode 7 as described above, the sticky sheet piece 8 of the electrode 7 is first applied to the skin surface M of the living body, as shown in FIG. 7, and then the lead connector 13 is coupled to the electrode 7 by bonding the magnetic electrode coupler 15 of the lead connector 13 to the lead coupler 11 of the electrode 7. In this state, a weak current from the heart, derived through the electrode plate 12, is led through the lead 16 to the electrocardiogram.

Usually, a weak current derived from the skin surface of a patient with a serious cardiac disease in a ward of a hospital through the electrode 7 held in close contact with the skin surface of the patient is led to an electrocardiogram installed in a separate nurse station to be checked by staff members.

However, the lead connector 13 which is coupled to the electrode 17 held in close contact with the patient's skin surface is liable to be shifted from a proper position with respect to the electrode 7 due to an unconscious movement of the patient such as tossing-about in sleep. In such a case, noise is produced, and an accurate electrocardiograph cannot be obtained.

Further, it is possible that the patient would unconsciously pull out the lead 16 of the lead connector 13 from the electrode 7. When the lead connector 13 is detached, an alarm device provided in the nurse station is activated. In this case, the staff members have to hasten to the patient's ward to check the patient's condition.

The alarm device is designed to produce an alarm in an emergency case such as when the pulsation of the heart of a patient is stopped during recording of the patient's electrocardiograph with the electrode 7 held in close contact with the patient's skin surface. With a detachment of the lead connector 13 or electrode 7 from the patient's skin, the alarm device also activated in spite of the fact that the patient's heart is normal. Even in such a case, the staff members have to hasten from the nurse station to the patient's ward. If the alarm device is frequently erroneously activated, the fatigue of the staff members is increased.

Further, in some cases an electrocardiogram of a patient is recorded while the patient is in motion, depending on the patient's condition. In this case, possible shift or detachment of the lead connector 13 coupled to the electrode held in close contact with the patient's skin surface, which detachment may be caused by a patient's motion, will disable the recording of an accurate electrocardiograph.

SUMMARY OF THE INVENTION

An object of the invention is to solve the problems discussed above in the prior art.

To attain the above object of the invention, there is provided an electrode securement sheet, which comprises a substantially circular, extensible porous electrode securement section secured to the skin surface of a living body to cover an electrode held in close contact with the skin surface for deriving a weak current from the living body. A lead securement section integrally extends from the electrode securement section for securing to the skin surface, a lead for leading the weak current extracted through the, electrode to an electrocardiograph. There is also provided a substantially rectangular lead securement piece and a cardboard, the electrode securement section with the lead securement section and the lead securement piece being separably bonded to the cardboard. The cardboard has separation assisting lines provided in portions corresponding to the electrode securement section, lead securement section and lead securement piece for facilitating the separation of these securement sections from the cardboard.

DETAILED DESCRIPTION OF THE PREFERRED EMBODIMENT

Figure 1:
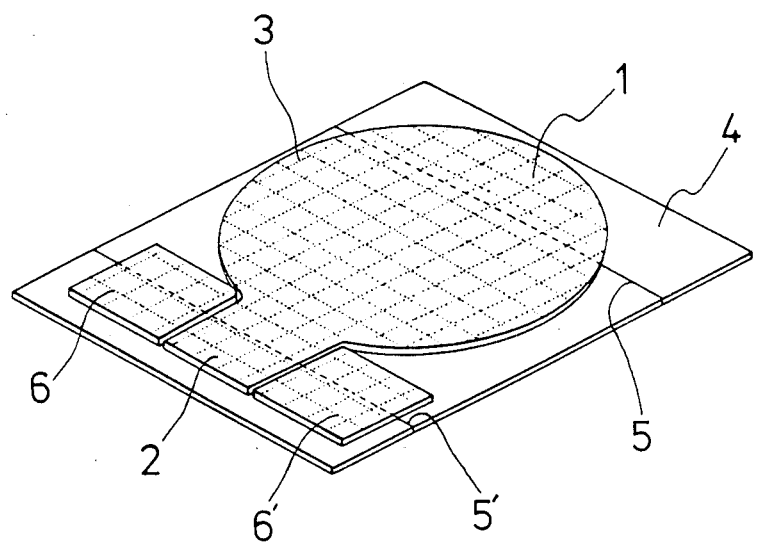
FIG. 1 is a perspective view showing an embodiment of the electrode securement sheet according to the invention.
Figure 2:
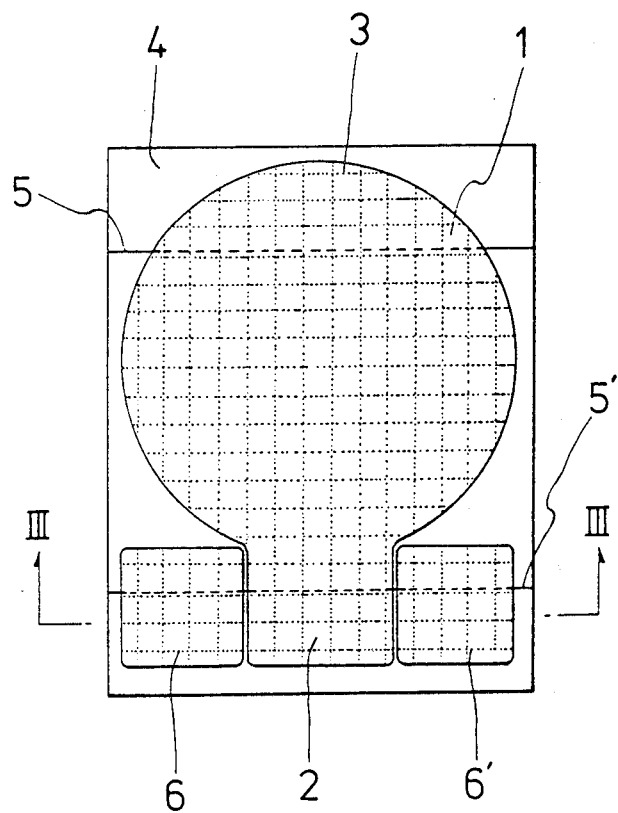
FIG. 2 is a plan view showing the electrode securement sheet shown in FIG. 1.
Figure 3:
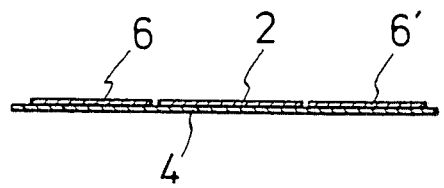
FIG. 3 is a sectional view taken along line III—III in FIG. 2.

FIG. 1 is a perspective view showing an embodiment of the electrode securement sheet according to the invention, FIG. 2 is a plan view of the same electrode securement sheet, and FIG. 3 is a sectional view taken along line III—III shown in FIG. 2. Referring to the figures, reference numeral 1 designates a substantially circular electrode securement section, which is adapted to be secured to the skin surface of a living body to cover the electrode 7 noted above, held in close contact with the skin surface of the living body to derive a weak current therefrom.

The electrode securement section 1 consists of a polyvinyl chloride sheet having a size sufficient to cover the electrode 7. It is porous, having numerous ventilating pores 3. This has an effect of preventing the electrode securement section 1 from being detached from the skin surface of the living body due to moistening of the section 1 caused by the action of sweating of the skin of the living body. The electrode securement section 1 is extensible, so that it can be readily attached to the skin surface by slightly stretching it. Also, it can be difficult detach after it has been attached.

The electrode securement section 1 has a rectangular lead securement 2 extending from one end. The lead securement portion 2 is made from the same porous and extensible polyvinyl chloride sheet.

The electrode securement section 1 and lead securement portion 2 may be made from a porous nonwoven cloth or from a porous braided sheet as well as from the porous polyvinyl chloride resin sheet.

Reference numeral 4 designates a thick cardboard. The electrode securement section 1 and lead securement portion 2 are separately bonded by an adhesive to the cardboard 4.

The cardboard 4 has two transversal separation assisting lines 5 and 5'. By virtue of the separation line 5, the electrode securement section 1 can be easily separated from the cardboard 4. The second transversal separation assisting line 5' is formed in a portion of the cardboard where the lead securement section 2 is bonded. By virtue of this separation assisting line 5', the lead securement section 2 can be readily separated from the cardboard 4. The presence of the separation assisting line 5' is particularly effective since the lead securement section 2 is smaller in size and hence more difficult to separate.

Lead securement pieces 6 and 6' are further bonded to the cardboard 4 separately from the electrode securement section 1 and lead securement section 2. The lead securement pieces 6 and 6' are used to secure a portion of the lead 16 extending from a stem portion thereof secured by the lead securement section 2, thus more firmly securing the lead 16 to the skin surface of the living body.

The lead securement pieces 6 and 6' are made from the same porous extensible material as the lead securement section 2. They are provided on the opposite sides of the lead securement section 2 and crossed by the separation assisting line 5'.

Figure 4:
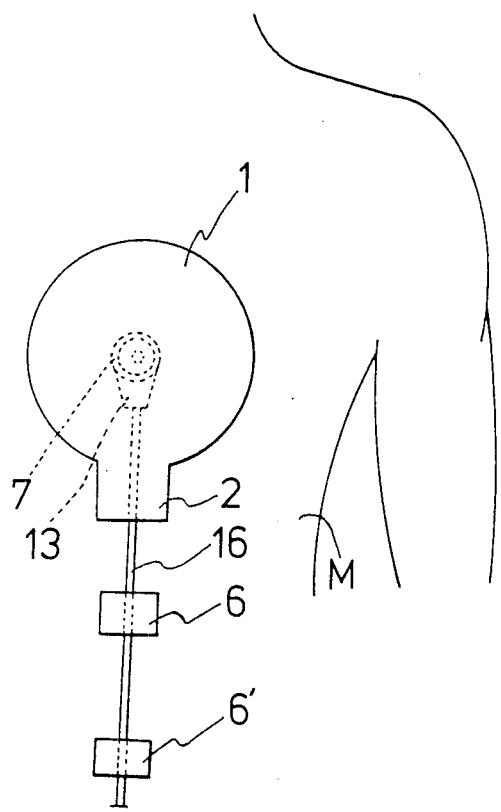
FIG. 4 is a view showing the electrode securement sheet according to the invention in use.
Figure 5:
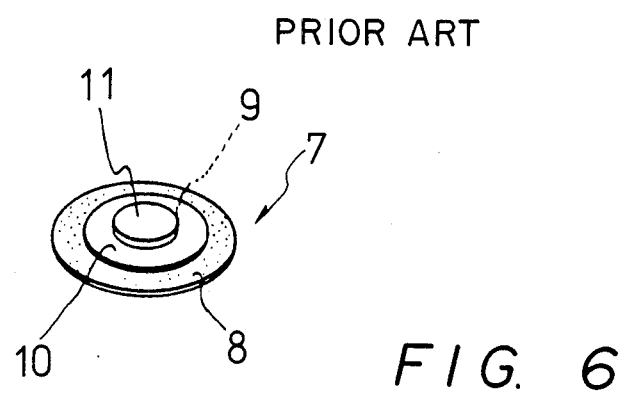
FIG. 5 is a perspective view showing a prior art electrode for deriving current from a living body.
Figure 6:
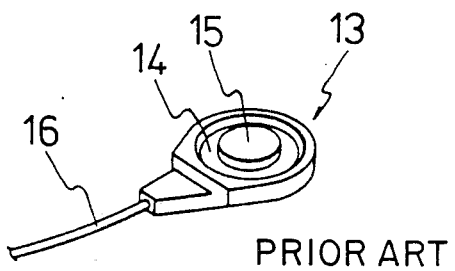
FIG. 6 is a view showing a lead connector.
Figure 7:
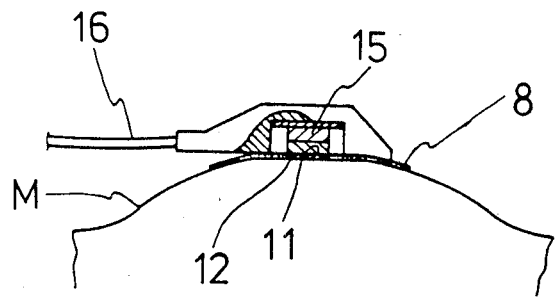
FIG. 7 is a view for explaining the electrode and lead connector in use.

The electrode securement sheet having the above construction is used as follows. As shown in FIG. 4, the electrode 7 is set on the skin surface M of a man in close contact therewith. Then, the lead connector 13 is coupled to the top of the electrode 7. Thereafter, the sheet-like electrode securement section 1 is readily separated by utilizing the separation assisting line 5 as shown in FIGS. 1 and 2, and is applied to the skin M to cover the entire electrode 7, to which the lead connector 13 is coupled, as shown in FIG. 4. Further, the sheet-like lead securement section 2 can be readily separated by virtue of the separation assisting line 5', and is applied to the skin M to cover the stem portion of the lead 16. Further, the lead securement pieces 6 and 6' can be readily separated by virtue of the separation assisting line 5' for being applied to the skin M to cover the end portion of the lead 6 extending from the stem thereof. Thus, the lead 16 can be completely secured to the skin M.

As has been described in the foregoing, according to the invention the electrode for extracting a current from a living body is secured to the skin surface thereof by the electrode securement section with a lead securement portion. The electrode thus is firmly held in close contact with the skin of a man and will never be detached therefrom during examination. It is thus possible to eliminate erroneous operations of the alarm device installed in the nurse station and reduce fatigue of the staff.

Further, since the electrode is firmly held in close contact with the skin surface of a man by the electrode securement section with the lead securement portion, it will never be shifted or detached even in case of recording an electrocardiograph while the patient is in motion. Such an electrocardiograph thus can be readily obtained.

Further, since the electrode securement section and lead securement section are integral with each other, the electrode securement sheet according to the invention can be secured to the skin in a single operation. The electrode securement sheet thus can save time and has satisfactory operability.

Further, since the separation assisting lines are provided in portions of the cardboard corresponding to the electrode securement section and lead securement section, the electrode securement section and lead securement section can be readily separated from the cardboard.

Further, since the lead securement pieces are separately bonded to the cardboard separately from the electrode securement section and lead securement section, not only the stem portion of the lead but also the end portion thereof extending from the stem portion can be secured, so that the lead can be perfectly secured to the skin surface of the living body.

Further, since the electrode securement section, lead securement section and lead securement pieces are all porous, they will not be moistened by the action of sweating of the skin when it is in close contact therewith, thus eliminating the possibility of detachment from the skin due to moistening. Further, since the electrode securement sheet is extensible, it is attached to the skin surface by slightly stretching it. Thus, it can be held in satisfactory close contact with the skin surface.

What is claimed is:
1. An electrode securement sheet comprising:
   a substantially circular, extensible porous electrode securement section for covering an electrode and for securing said electrode to the skin surface of a living body, said electrode being held in close contact with the skin surface for deriving a weak current from said living body;

a lead securement section integrally extending from said electrode securement section for securing, to the skin surface, a lead for leading the weak current extracted through said electrode to an electrocardiogram;

a substantially rectangular lead securement piece provided separately from said electrode securement section and said lead securement section; and a cardboard having separately bonded thereon said electrode securement section with said lead securement section and said lead securement piece, said cardboard having separation assisting lines provided in portions corresponding to said electrode securement section, lead securement section and lead securement piece for facilitating the separation of these securement sections and piece from said cardboard.

2. The electrode securement sheet according to claim 1, wherein said electrode securement section, lead securement section and lead securement piece consist of a porous resin sheet.

3. The electrode securement sheet according to claim 1, wherein said electrode securement section, lead securement section and lead securement piece consist of a porous non-woven cloth.

4. The electrode securement sheet according to claim 1, wherein said electrode securement section, lead securement section and lead securement piece consist of a porous woven cloth.

5. The electrode securement sheet according to claim 1, wherein said lead securement piece is provided adjacent to one side of said lead securement section and separately bonded to said cardboard.

* * * * *

UNITED STATES PATENT AND TRADEMARK OFFICE
CERTIFICATE OF CORRECTION

PATENT NO. : 4,653,502
DATED : March 31, 1987
INVENTOR(S) : Hirokatsu Inoue, et al.

It is certified that error appears in the above—identified patent and that said Letters Patent is hereby corrected as shown below:

Column 2, line 17, change "activated" to --activates--;

Column 2, line 18, delete the comma;

Column 3, line 26, after "difficult" insert --to--.

Signed and Sealed this

Twenty-second Day of September, 1987

Attest:

DONALD J. QUIGG

Attesting Officer   Commissioner of Patents and Trademarks